US011484556B2

(12) United States Patent
Everett et al.

(10) Patent No.: US 11,484,556 B2
(45) Date of Patent: *Nov. 1, 2022

(54) NUTRIENT RICH GERMINANT COMPOSITION AND SPORE INCUBATION METHOD

(71) Applicant: NCH Corporation, Irving, TX (US)

(72) Inventors: Gabriel F. K. Everett, Coppell, TX (US); Charles Greenwald, Dallas, TX (US); Judy Pruitt, Mesquite, TX (US); Amanda Rosmarin, Lantana, TX (US); Jordan Church, Dallas, TX (US); Daniel Aberle, Irving, TX (US); George Aboagye, Derby (GB)

(73) Assignee: NCH Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/785,138

(22) Filed: Feb. 7, 2020

(65) Prior Publication Data

US 2020/0171104 A1    Jun. 4, 2020

Related U.S. Application Data

(62) Division of application No. 15/479,773, filed on Apr. 5, 2017, now Pat. No. 10,610,552.

(60) Provisional application No. 62/318,587, filed on Apr. 5, 2016.

(51) Int. Cl.
| | |
|---|---|
| *A61K 35/742* | (2015.01) |
| *A61K 47/02* | (2006.01) |
| *C12N 3/00* | (2006.01) |
| *C02F 3/34* | (2006.01) |
| *C12N 1/04* | (2006.01) |
| *C12N 1/20* | (2006.01) |
| *A23L 29/00* | (2016.01) |
| *C12R 1/01* | (2006.01) |
| *C12R 1/07* | (2006.01) |
| *C12R 1/125* | (2006.01) |

(52) U.S. Cl.
CPC .......... *A61K 35/742* (2013.01); *A23L 29/065* (2016.08); *A61K 47/02* (2013.01); *C02F 3/34* (2013.01); *C02F 3/348* (2013.01); *C12N 1/04* (2013.01); *C12N 1/20* (2013.01); *C12N 1/205* (2021.05); *C12N 3/00* (2013.01); *C12R 2001/01* (2021.05); *C12R 2001/07* (2021.05); *C12R 2001/125* (2021.05)

(58) Field of Classification Search
None
See application file for complete search history.

(56) References Cited

U.S. PATENT DOCUMENTS

| | | |
|---|---|---|
| 5,501,857 A | 3/1996 | Zimmer |
| 6,327,965 B1 | 12/2001 | Tien |
| 6,335,191 B1 | 1/2002 | Kiplinger et al. |
| 6,461,607 B1 | 10/2002 | Farmer |
| 6,849,256 B1 | 2/2005 | Farmer |
| 7,081,361 B2 | 7/2006 | Pearce, III et al. |
| 7,736,509 B2 | 6/2010 | Kruse |
| 7,754,469 B2 | 7/2010 | Baltzley et al. |
| 8,192,733 B2 | 6/2012 | Cobb et al. |
| 8,349,337 B1 | 1/2013 | Farmer et al. |
| 8,506,951 B2 | 8/2013 | Rehberger et al. |
| 8,540,981 B1 | 9/2013 | Wehnes et al. |
| 8,551,762 B2 | 10/2013 | Fleming et al. |
| 8,647,690 B2 | 2/2014 | Corrigan |
| 8,822,208 B2 | 9/2014 | Chokshi |
| 9,011,834 B1 | 4/2015 | McKenzie et al. |
| 9,447,376 B2 | 9/2016 | Hashman et al. |
| 9,932,543 B2 | 4/2018 | Hashman et al. |
| 2003/0165472 A1 | 9/2003 | McGrath et al. |
| 2003/0228679 A1 | 12/2003 | Smith et al. |
| 2004/0232069 A1 | 11/2004 | Shaffer |
| 2005/0255092 A1 | 11/2005 | Rehberger et al. |

(Continued)

FOREIGN PATENT DOCUMENTS

| | | |
|---|---|---|
| CA | 2778144 | 5/2011 |
| CN | 1528681 | 9/2004 |

(Continued)

OTHER PUBLICATIONS

Soni et al. Food and Chemical Toxicology 39 (2001) 513-532.*

(Continued)

*Primary Examiner* — Oluwatosin A Ogunbiyi
(74) *Attorney, Agent, or Firm* — Scheef & Stone, LLP; Robin L. Barnes

(57) ABSTRACT

A nutrient-germinant composition to aid in spore germination and a method for increased spore germination efficiency. The composition comprises L-amino acids, D-glucose and/or D-fructose, a phosphate buffer, an industrial preservative, and may include bacteria spores or they may be separately combined for germination. The method comprises providing a nutrient-germinant composition and bacteria spores, preferably of one or more *Bacillus* species, and heating to a preferred elevated temperature range of 41° C. to 44° C. for an incubation period of around 2 to 60 minutes. The nutrient-germinant composition is preferably in a concentrated liquid form that is diluted just prior to initiating the germination/incubation method at the point of use. The method may also include dispensing a germinated spore solution to a point-of-use/consumption, such as animal feed, water, or bedding, or a wastewater system or drain.

48 Claims, 3 Drawing Sheets

(56) References Cited

U.S. PATENT DOCUMENTS

| | | |
|---|---|---|
| 2008/0241226 A1 | 10/2008 | Abeln et al. |
| 2009/0186057 A1 | 7/2009 | Farmer et al. |
| 2009/0232941 A1 | 9/2009 | Farmer |
| 2009/0242173 A1 | 10/2009 | Mitchell |
| 2010/0124586 A1 | 5/2010 | Becker |
| 2011/0230345 A1 | 9/2011 | Snyder et al. |
| 2011/0256216 A1 | 10/2011 | Lefkowitz |
| 2012/0034344 A1 | 2/2012 | Menon |
| 2012/0052152 A1 | 3/2012 | Armentrout |
| 2012/0100094 A1 | 4/2012 | Reuter et al. |
| 2013/0092087 A1 | 4/2013 | Bachman et al. |
| 2013/0171204 A1 | 7/2013 | DuBourdieu |
| 2014/0295482 A1 | 10/2014 | Lyte |
| 2015/0079661 A1 | 3/2015 | Pruitt |
| 2015/0299636 A1 | 10/2015 | Tutkimuskeskus |
| 2015/0333828 A1 | 11/2015 | Greenwald et al. |
| 2015/0336828 A1 | 11/2015 | Greenwald et al. |
| 2016/0113289 A1 | 4/2016 | Patel |
| 2017/0087199 A1* | 3/2017 | Patron ............... A61K 36/81 |

FOREIGN PATENT DOCUMENTS

| | | | |
|---|---|---|---|
| CN | 102329765 A * | 1/2012 | ............ C12P 13/06 |
| WO | WO1999005310 | 2/1999 | |
| WO | WO-03029783 A1 * | 4/2003 | ............ G01N 1/30 |
| WO | WO2004024865 | 3/2004 | |
| WO | WO-2009081276 A2 * | 7/2009 | .......... C08B 37/006 |
| WO | WO2009126473 | 10/2009 | |
| WO | WO2010045541 | 4/2010 | |
| WO | WO2010066012 | 6/2010 | |
| WO | WO2012079973 | 6/2012 | |
| WO | WO2013142792 | 9/2013 | |
| WO | WO2014193746 | 12/2014 | |
| WO | WO-2015038892 A1 * | 3/2015 | .......... A61K 31/198 |
| WO | WO2016044661 | 3/2016 | |
| WO | WO2017117089 | 7/2017 | |

OTHER PUBLICATIONS

Mohan, Chandra. Calbiochem Buffers. A guide for the preparation and use of buffers in biological systems. 2003.*

Handbook of Pharmaceutical Excipients, Pharmaceutical Press, 2009. pp. 766-770.*

Madslien, Elisabeth H.; Granum, Per Einar; Blatny, Janet M; and Lindback, Toril, L-alanine-induced germination in Bacillus licheniformis—the impact of native gerA sequences, BMC Microbiology, published 2014, p. 1-10.

Martin, J. H. and Harper, W. J., Germination Response of Bacillus Licheniformis Spores to Amino Acids, Department of Dairy Technology, Journal of Dairy Science, Jul. 1963, p. 663-667.

Setlow, Peter, Summer Meeting 2013—when the sleepers wake: the germination of spores of Bacillus species, Journal of Applied Microbiology, Sep. 2013, p. 1251-1268.

Sinai, Lior; Rosenberg, Alex; Smith, Yoav; Segev, Einat; and Ben-Yehuda, Sigal, The Molecular Timeline of a Reviving Bacterial Spore, Molecular Cell, Feb. 2015, p. 695-707.

Yasuda, Yoko and Tochikubo, Kunio, Relation between D-Glucose and L- and D-Alanine in the Initiation of Germination of Bacillus subtilis Spore, Microbio. Immunol. Oct. 1983, p. 197-207, vol. 28. No. 2.

Cutting, Simon M., Bacillus Probiotics, Food Microbiology, 2011, vol. 28, pp. 214-220.

Chedia, Aquadhi et al., Optimization of nutrient-induced germination of Bacillus sporothermodurans spores using response surface methodology, Food Microbiology, Academic Press Ltd, V. 36, N. 2, Jul. 8, 2013, pp. 320-326.

Ramirez-Peralta, Arturo et al., Effects of 1-16 sporulation conditions on the germination and germination protein levels of Bacillus subtilis spores, Applied and Environmental Microbiology Apr. 2012, V. 78, N. Apr. 8, 2012, pp. 2689-2697.

Wang, Shiwei et al., Slow Leakage of Ca-Dipicolinic Acid from Individual Bacillus Spores during Initiation of Spore Germination, Journal of Bacteriology, V. 197, N. 6, Mar. 2015, pp. 1095-1103.

Luu, Stephanie, et al., The Effects of Heat 1-16 Activation on Bacillus Spore Germination, with Nutrients or under High Pressure, with or without Various Germination Proteins, Applied and Environmental Microbiology, V. 81, N. 8, Feb. 13, 2015, pp. 2927-2398.

Timmermann et al., Metabolism and Nutrition Mortality and Growth Performance of Broilers Given Drinking Water Supplemented with Chicken-Specific Probiotics, Poultry Science, vol. 85, Aug. 1, 2006, pp. 1383-1388.

Katsutoshi et al., Effect of spore-bearing lactic acid-forming bacteria (Bacillus coagulans SANK 70258) administration on the intestinal environment, defecation frequency, fecal characteristics and dermal characteristics in humans and rats, Microbial Ecology in Health & Dis, Co-Action Publishing, SE, vol. 14, No. 1, Mar. 2002, pp. 4-13.

Casula, G and S. Cutting. 2002. Bacillus Probiotics: Spore Germination in the Gastrointestinal Tract. American Society for Microbiology. vol. 68, No. 5: 2344-2352.

Wikipedia, "Sodium chloride", Nov. 1, 2017, retrieved on Apr. 5, 2019 from https://en.wikipedia.org/w/index.php?title=Sodium_chloride&oldid=808219406, pp. 1-9.

Gurung, Neelam, et al., A Broader View: Microbial Enzymes and Their Relevance in Industries, Medicine, and Beyond, BioMed Research International; vol. 2013, Article ID 329121.

Yazdi, Mohammed A., et al., Characterization and cloning of the gerC locus of Bacillus subtilis 168, Journal of General Microbiology, 1990, 136, 1335-1342.

EcoBionics Biological System Data Sheet, believed to be published at least as early as 2016 (relates to Bioamp).

Waites, The Effect of pH, Germinants and Temperature on the Germination of Spores of Clostridium bifermentans, Journal of General Microbiology, 1974, 80, 253-258 (Year: 1974).

Nguyen, Bacillus subtilis spores expressing the VP28 antigen; a potential oral treatment to protect Litopenaeus vannamei against white spot syndrome, FEMS Microbiilogy Letters Sep. 1, 2014 (Sep. 1, 2014), vol. 358, pp. 202-208, p. 203.

Shearer et al., Bacterial Spore Inhibition and Inactivation in Foods by Pressure, Chemical Preservatives, and Mild Heat, Journal of Food Protection, Nov. 2000, vol. 63, pp. 1503-1510, p. 1504-1505.

Setlow, Germination of Spores of Bacillus Species, What We Know and Do Not Know, Journal of Bacteriologoy, Apr. 2014, vol. 196, pp. 1297-1305, p. 1298.

American Society of Agronomy (ASA), Crop Science Society of America (CSSA). "Probiotics—for plants." ScienceDaily ScienceDaily, Jul. 8, 2015 Jul. 8, 2015.

Joint FAO/WHO Expert Consultation on Evaluation of health and nutritional properties of probiotics in food including powder milk with live lactic acid bacteria, Cordoba, Argentina. Oct. 1-4, 2001 Oct. 1, 2001.

Kumar et al., Bacillus as PGPR in crop ecosystem; Bacteria in agrobiology: crop ecosystems. Springer Berlin Heidelberg, 37-59, 2011 2011.

Wax, R. et al. Separation of Two Functional Roles of L-Alanine In the Initiation of Bacillus subtilis Spore Generation. J of Bacteriology 94(3)522-529, Sep. 1967 (Year: 1967).

Wuytack, E. et al. Comparative Study of Pressure and Nutrient Induced Germination of Bacillus subtilis Spores. Applied and Environmental Microbiology 66(1)257-261. Jan. 2000. (Year: 2000).

Bergeys Manual of Systematics Archaea and Bacteria, John Wiley & Sons, Bacillus chapter 1-164, 2015 (Year: 2015).

* cited by examiner

NUTRIENT RICH GERMINANT COMPOSITION AND SPORE INCUBATION METHOD

CROSS REFERENCE TO RELATED APPLICATION

This application is a divisional of U.S. application Ser. No. 15/479,773 filed on Apr. 5, 2017, now U.S. Pat. No. 10,610,552, which claims the benefit of U.S. provisional patent application No. 62/318,587 filed Apr. 5, 2016.

BACKGROUND OF THE INVENTION

1. Field of the Invention

The present invention relates to a nutrient-germinant concentrate composition and a point-of-use incubation method of germinating bacterial spores.

2. Description of Related Art

Spore germination is a multistep, causative process wherein spores effectively wake-up or are revived from a dormant state to a vegetative growth state. The first step is one by which spores are activated and are induced to germinate, typically by an environmental signal called a germinant. This signal can be a nutrient such as an L-amino acid. Nutrient germinants bind to receptors in the inner-membrane of the spore to initiate germination. Additionally, sugars have been shown to increase the binding affinity of L-amino acids for their cognate receptors.

The germinant signal then initiates a cascade that causes the release of Dipicolinic Acid (DPA), which is stored in a 1:1 ratio with $Ca^{2+}$ (CaDPA) in the core of the spore. The release of CaDPA is a fast process and is typically >90% complete in 2 min. CaDPA release represents a point of no return for spores in which they are committed to the germination process. Those knowledgeable in the art refer to this step as the "commitment" step.

After CaDPA release, the spore is partially hydrated and the core pH rises to approx. 8.0. The core of the spore then expands and the cortex (composed mostly of peptidoglycan) is degraded by core lytic enzymes. The spore absorbs water and consequently loses its refractivity. This loss of refractivity towards the end of the germination process allows spore germination to be monitored via phase-contrast microscopy.

The second phase of germination is an outgrowth step in which the spore's metabolic, biosynthetic, and DNA replication/repair pathways initiate. The outgrowth period has several phases. The first is known as a ripening period in which no morphological changes (such as cell growth) occur, but the spore's molecular machinery (e.g. transcription factors, translation machinery, biosynthesis machinery, etc.) is activated. This period can vary in length based on the initial resources that are packaged with the spore during the process of sporulation. For instance, the preferred carbon source of several Bacillus species (including subtilis) is malate and Bacillus spores typically contain a large pool of malate that is used during the revival process. Interestingly, deletion mutants that cannot utilize the malate pool display an extended ripening period compared to wild-type spores indicating that the spore malate pool is sufficient to energize the initial outgrowth process. Additionally, spores store small, acid-soluble proteins that are degraded within the first several minutes of revival that serve as an immediate source of amino acids for protein synthesis. After the outgrowth step, spore revival is complete and cells are considered to be vegetatively growing.

It is known that spores can be induced to germinate via heat-activation. Spores of various Bacillus species have been heat-activated at strain-specific temperatures. For example, B. subtilis spores have been heat-activated at 75° C. for 30 minutes while B. licheniformis spores have been heat-activated at 65° C. for 20 minutes. The heat-activation has been shown to cause a transient, reversible unfolding of spore coat proteins. Heat-activated spores can then be germinated for additional time in germination buffers containing nutrient germinants, such as L-alanine. If no nutrient germinant is present, however, spores will return to their pre-heated, non-germinated state.

It is also known that germination can occur at ambient temperatures (near typical room temperature) without heat-activation and with a germination buffer containing nutrients, but the process usually takes longer than with heat-activation. For example, B. licheniformis and B. subtilis spores will germinate at 35° C. or 37° C., respectively, but it takes a longer period of time (e.g. 2 hours) in a germination buffer containing nutrient germinants. Additionally, non-heat-activated spores of B. subtilis have been known to have been germinated in non-nutrient germinant conditions (e.g. $CaCl_2+Na_2DPA$) for an extended period of time.

It is also known to combine the use of heat activation and a nutrient germinant to germinate spores in a two-step process in laboratory settings. The spores are first heat activated by incubating for a period of time (e.g. 30 minutes) at a temperature in the range of 65-75° C. (this specific temperature is species dependent). Then, the spores are transferred into a buffer solution that contains a nutrient germinant, such as L-alanine. It is also known to grow bacteria in a growth chamber located near a use site by feeding pelletized nutrient material (containing sugar, yeast extract, and other nutrients that are not direct spore germinants), bacteria starter, and water into a growth chamber at a controlled temperature range of 16-40° C., and more preferably between 29-32° C., for a growth period of around 24 hours as disclosed in U.S. Pat. No. 7,081,361.

There is a need for a rapid spore incubation and activation method that will allow generation of active Bacillus species in a single step at a point-of-use location where the bacteria will be distributed to a consumer/user, for example, in the way of a probiotic for use in human, animal or plant consumption or directly into a water treatment facility or a drain line. Accordingly, this invention describes a simple method for spore germination using a nutrient germinant concentrate simultaneously with heat incubation in a single step.

SUMMARY OF THE INVENTION

A nutrient-germinant composition according to one preferred embodiment of the invention comprises one or a combination of many L-amino acids, optionally D-glucose (which increases the binding affinity of L-amino acids for their cognate receptors in the spore coat), and a neutral buffer such as a phosphate buffer, and an industrial preservative, such as the commercially available Kathon/Lingaurd CG (which has active ingredients comprising methyl chloro isothiazolinone and methyl isothiazolinone). A nutrient-germinant composition according to another preferred embodiment of the invention comprises one or a combination of two or more L-amino acids, optionally D-glucose (which increases the binding affinity of L-amino acids for their cognate receptors in the spore coat), HEPES sodium salt (a biological buffer to provide the proper pH for spore germination), and an industrial preservative, such as a combination of propylparaben and methylparaben or other GRAS (Generally Regarded As Safe) preservatives. According to another preferred embodiment, the composition also comprises a source of potassium ions, such as potassium chloride or monopotassium phosphate or dipotassium phosphate. According to another preferred embodiment, the composition includes both D-glucose and D-fructose.

According to another preferred embodiment, the composition also comprises spores of one or more *Bacillus* species and includes a germination inhibitor, such as NaCl, industrial preservatives, or D-alanine, in combination with any of the previously described composition ingredients. The germination inhibitor prevents the spores from germinating prematurely in the nutrient-germinant composition. The germination inhibitor may include chemicals that prevent spore germination such as NaCl, industrial preservatives, or D-alanine. Alternatively, bacterial spores may be separately provided and added to a nutrient-germinant composition according to the invention at the point-of-use and incubation.

According to another preferred embodiment, a nutrient germinant composition according to the invention is in concentrated form and is diluted to 0.01% to 10% strength in water or another diluent at the point-of-use. The use of a concentrated formula reduces shipping, storage, and packaging costs and makes dosing of the composition at the point-of-use easier. Most preferably, the concentrated composition is in a liquid form, which is easier and faster to mix with diluent at the point-of-use, but solid forms such as pellets or bricks or powder may also be used. The inclusion of a general, industrial preservative in the composition aids in long-term storage and/or germination inhibition, which is particularly useful when the composition is in the preferred concentrated form.

In another preferred embodiment, the present invention comprises a method of germinating spores of *Bacillus* species using a nutrient germinant composition at an elevated temperature; preferably in a range of 35-60° C., more preferably in the range of 38-50° C., and most preferably in the range of 41° C. to 44° C. for a period of time (an incubation period). The incubation period preferably ranges from 2-60 minutes, depending on the application. Most preferably, a nutrient-germinant composition in concentrated form according to a preferred composition of the invention is used in the incubation methods of the invention, but other nutrient-germinant compositions may also be used. Preferably, the incubation method is carried out at or near the point-of-use—the site or near the site where the germinated spores will be used (such as near animal feeding, watering, or bedding sites) or consumed and further comprises dispensing the germinated spores to the point-of-use/consumption. Preferred methods according to the invention may be carried out in any incubation device that has a reservoir capable of holding a volume of spores, liquid (typically water), nutrient-germinant composition and that is capable of heating the mixture during an incubation period. Most preferably, the methods are carried out in a device that is also capable of mixing those ingredients, automatically shutting-off heating at the end of the incubation period, and automatically dispensing a probiotic or treatment solution comprising the spores to a point-of-use/consumption. Preferred methods may also be carried out as a batch process or as a continuous process. Any variety of spore forms, such as dried powder form, a liquid suspension, or a reconstituted aqueous mixture, may be used with the method of the invention.

The preferred embodiments of the invention have broad utility and application and will allow for rapid germination of spores of *Bacillus* species at a point-of-use. The preferred embodiments are particularly useful in preparing spores for use as a probiotic, for feeding to animals for example, and for providing bacteria to treat wastewater systems or provide drain maintenance.

BRIEF DESCRIPTION OF THE DRAWINGS

The invention is further described and explained in relation to the following drawings wherein.

DESCRIPTION OF THE PREFERRED EMBODIMENTS

Figure 1:
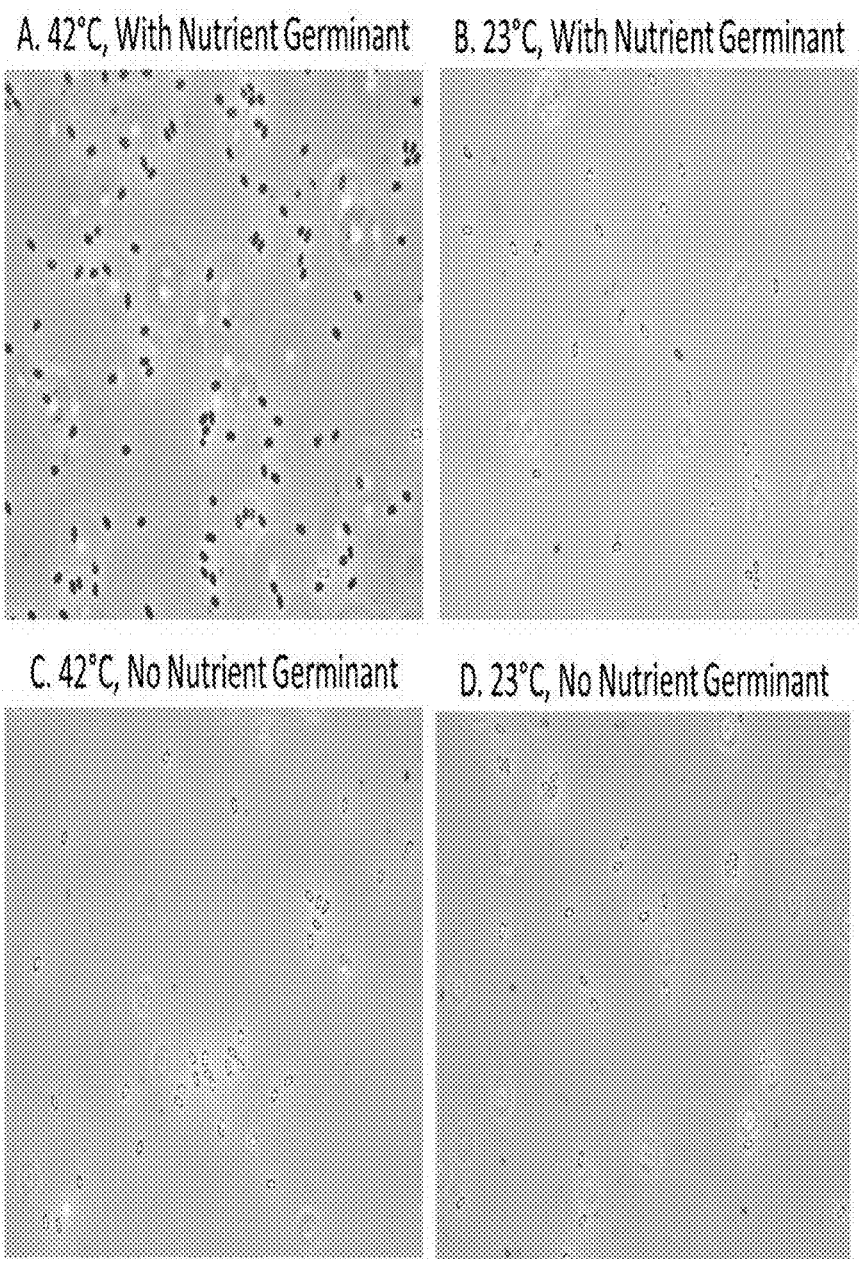
FIG. 1 shows photographs of bacteria slides using a composition and method according to a preferred embodiment of the invention compared to control slides.

A nutrient-germinant composition according to one preferred embodiment of the invention comprises one or more L-amino acids, D-glucose (which increases the binding affinity of L-amino acids for their cognate receptors in the spore coat and is optional), D-Fructose (optional, depending on bacteria species), a biological buffer to provide the proper pH for spore germination (such as HEPES sodium salt, a phosphate buffer, or a Tris buffer), an optional source of potassium ions (such as KCl), and an industrial preservative. In another preferred embodiment, the composition comprises both D-glucose and D-fructose. It is most preferred to include a source of potassium ions, such as KCl, when both D-glucose and D-fructose are used. The use of D-fructose, a combination of D-glucose and D-fructose, and a potassium ion source are dependent on the species of bacteria as will be understood by those of ordinary skill in the art. It is preferred to use a preservative that is pH compatible with the composition, which has a relatively neutral pH. According to another preferred embodiment, the composition also comprises spores of one or more *Bacillus* species and one or more germination inhibitors. Alternatively, spores may be separately added to the nutrient-germinant composition according to the invention at the point-of-use. According to another preferred embodiment, the composition is in a concentrated form, most preferably as a concentrated liquid, and is diluted at the point-of-use.

Preferred L-amino acids include L-alanine, L-asparagine, L-valine, and L-cysteine. In a further embodiment of the concentrate composition, L-amino acids can be provided as a hydrolysate of soy protein. When in a concentrated form, the composition preferably comprises a solution of one or more of the above mentioned L-amino acids in the weight range of 8.9-133.5 g/L, more preferably 13.2-111.25 g/L, and most preferably 17.8-89 g/L each; D-glucose (optional) and/or D-fructose (optional) in the weight range of 18-54 g/L, more preferably 27-45 g/L, and most preferably 30-40 g/L each; KCl (optional, as a source of potassium) in the weight range of 7.4-22.2 g/L, more preferably 11.1-18.5 g/L, and most preferably 14-16 g/L; monosodium phosphate in a weight range of 10-36 g/L, more preferably 15-30 g/L, and most preferably 20-24 g/L; disodium phosphate in a weight range of 30-90 g/L, more preferably 21.3-75 g/L, and most preferably 28.4-60 g/L; and an one or more industrial preservatives at a final (total) weight range of 0.8-3.3 g/L, more preferably 1.2-2.7 g/L, most preferably 1.6-2.2. In addition to or in place of the monosodium/disodium phosphate buffer, the composition may comprise Tris base in a weight range of 15-61 g/L, more preferably 24-43 g/L, and most preferably 27-33 g/L; or HEPES buffer in a weight range of 32.5 97.5 g/L, more preferably 48.75-81.25 g/L, and most preferably 60-70 g/L. Optionally, monopotassium phosphate may also be used as a source of potassium ions, preferably in a weight range of 13.6-40.8 g/L, more preferably 20.4-34 g/L, and most preferably 26-29 g/L. Optionally, dipotassium phosphate may also be used as a source of potassium ions, preferably in a weight range of 8.7-26.1 g/L, more preferably 13-21.75 g/L, and most preferably 16-19 g/L. The amounts of these ingredients are important aspects of the invention because higher concentrations would render some ingredients insoluble and lower concentrations would be ineffective at germinating spores.

Most preferably, a nutrient-germinant concentrate composition according to embodiments of the invention is in concentrated form and is diluted to a working solution in water or any other appropriate diluent, preferably at the point-of-use. The dilution is preferably in a range from 0.1-10% of the concentrate and the balance water, but other amounts may also be used. The use of a concentrated formula reduces shipping, storage, and packaging costs and makes dosing of the composition at the point-of-use easier. Most preferably, the concentrated composition is in a liquid form, which is easier and faster to mix with diluent at the point-of-use, but solid forms such as pellets or bricks or powder may also be used. The inclusion of a general, industrial preservative in the composition aids in long-term storage and/or germination inhibition, which is particularly useful when the composition is in the preferred concentrated form.

According to one preferred embodiment, the composition preferably comprises 10% to 90% by weight of one or more *Bacillus* spores. The preferred *Bacillus* spores include the following species: *Bacillus licheniformis, Bacillus subtilis, Bacillus amyloliquiefaciens, Bacillus polymyxa, Bacillus thuringiensis, Bacillus megaterium Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex*, and *Bacillus sphaericus*. Other *Bacillus* spore species may also be used as will be understood by those of ordinary skill in the art. Most preferably, the composition comprises 3 to 12 *Bacillus* species. Alternatively, these spores may be separately added to the nutrient-germinant composition at the point-of-use.

In another preferred embodiment, a nutrient-germinant composition for use as a probiotic comprises one or more *Bacillus* strains that are probiotic in nature in that they aid in the breakdown of nutrients in the digestive tract of the consumer. The strains preferably produce one or more of the following enzymes: proteases to hydrolyze proteins, amylases to hydrolyze starches and other carbohydrates, lipases to hydrolyze fats, glycosidases to assist in the hydrolysis of glycosidic bonds in complex sugars and to assist in degradation of cellulose, cellulases to degrade cellulose to glucose, esterase which is a lipase-like enzyme, and xylanases that degrade xylan, a polysaccharide found in plant cell walls. *Bacillus* strains that produce these enzymes are well known in the art. Alternatively, these *Bacillus* strains may also be separately added to the nutrient-germinant composition at the point-of-use.

In another embodiment, a nutrient-germinant composition for use as a wastewater treatment or a drain treatment comprises one or more *Bacillus* strains that produce enzymes that are beneficial in the digestion of organic matter typically found in wastewater and/or drains. The *Bacillus* strains preferably produce one or more of the following enzymes: proteases to hydrolyze plant and animal proteins, amylases to hydrolyze starches and other carbohydrates, lipases to hydrolyze vegetable and animal fats, oils, and grease, glycosidases to assist in the hydrolysis of glycosidic bonds in complex sugars and to assist in degradation of cellulose, cellulases to degrade cellulose to glucose, esterase which is a lipase-like enzyme, and xylanases. Other enzymes may be produced, as well. The particular *Bacillus* species selected for inclusion in a preferred composition according to the invention may be one that specifically produces enzymes targeted for the particular type of organic matter that is found in the wastewater and/or drain being treated. *Bacillius* strains that produce these enzymes or are targeted for particular types of waste treatment are well known in the art. Again, as another alternative, these *Bacillus* strains may also be separately added to the nutrient-germinant composition at the point-of-use.

When spores are included in the nutrient-germinant composition, the composition also comprises one or more germination inhibitors and/or preservatives. Preferred germination inhibitors or preservatives include NaCl, D-alanine, or preservatives. Specifically, the composition comprises a high concentration of NaCl in the range of 29-117 g/L, more preferably 43-88 g/L, most preferably 52-71 g/L, and/or one or more chemical preservatives (such as Linguard ICP or Kathon CG (which has active ingredients comprising methyl chloro isothiazolinone, around 1.15-1.18% and methyl isothiazolinone, around 0.35-0.4%)) at a final (total) concentration of 0.8-3.3 g/L, more preferably 1.2-2.7 g/L, most preferably 1.6-2.2 g/L, and/or D-alanine (a known competitive inhibitor of germination) in the range of 8-116 g/L, more preferably 26-89 g/L, most preferably 40-50 g/L. These germination inhibitors or preservatives maintain the spores in an inactive state and prevent premature germination of the spores prior to their dilution and activation at the point-of-use. The use of germination inhibitors is particularly preferred when the composition according to this embodiment is used with the preferred method of the invention, where germination occurs at the point-of-use. The nutrient-germinant composition according to the invention optionally comprises other standard ingredients including, but not limited to, other preservatives that ensure the shelf-life of the composition and surfactants that aid in the dispersal of active ingredients, that are typically included in spore compositions or in industrial treatment products.

According to one preferred embodiment, a method of germinating spores at a point-of-use according to the invention comprises providing a composition comprising spores and nutrients (preferably a composition according to the invention, but the spores and nutrients may also be in separate compositions/separately added components) and heating the composition to an elevated temperature or range of temperatures and maintaining the composition at that temperature or within that range for a period of time (incubation period) to allow germination at a point-of-use location near a point-of-consumption. Heating during the incubation period takes place in the presence of the nutrient-germination composition in a single step. The method also preferably comprises the step of dispensing the germinated spores to an animal (through feed or water), animal bedding, plants, ponds, humans, wastewater system, or drain. Preferably, the spore composition is heated to a temperature in a range of 35-55° C., more preferably in the range of 38-50° C., and most preferably in the range of 41° C. to 44° C. The incubation period can vary depending on the end-use application. For a probiotic application, it is preferred that the incubation period lasts no longer than 10 minutes. Most preferably, in a probiotic application, the incubation period is between 2-5 minutes. In this way, spores are released to the animal before the spores have fully germinated and stand a better chance of surviving through to the animal's intestinal tract where they are most beneficial. On the other hand, a wastewater application may require a longer incubation period ranging between 20-60 minutes to ensure that fully germinated spores are delivered to the wastewater being treated. Most preferably, the incubation period is between 20-30 minutes for wastewater treatment. Regardless of application, the incubation may be in an air incubator, a water incubator, or any other chamber that provides even, constant heat at the given temperature range.

Various compositions according to preferred embodiments of the invention were tested according to preferred methods of the invention. The compositions, methods, and results are described below.

Example 1

To germinate spores, FreeFlow LF-88 Probiotic (spore liquid formula commercially available from NCH Corporation) was added to 1 mL of tap water at a final concentration of approx. $1 \times 10^9$ CFU/mL, where CFU stands for colony forming unit. A nutrient germinant concentrate composition according to a preferred embodiment of the invention comprising L-alanine (89 g/L), monosodium phosphate (20 g/L), disodium phosphate (60 g/L), and Linguard CP (1.6 g/L total) was added to the water and bacteria mixture to provide a 4% final concentration of nutrient-germinant composition by total weight of the mixture. For comparison, negative control reactions were prepared with the same amount of FreeFlow LF-88 Probiotic and water, but without adding the nutrient germinant concentrate composition. Both mixtures (germinant and negative control without the nutrient-germinant composition) were blended and incubated for 60 minutes in a pre-incubated heat block set to 42° C. or at ambient room temperature (around 23° C.).

Spores from each reaction were observed using phase contrast microscopy. Slides were prepared using standard procedures. Spores were viewed on an Olympus BX41 microscope (100× oil emersion objective) and imaged using an Olympus UC30 camera controlled by the cellSens Dimension software package.

Images were taken and germinated spores were counted as a percentage of the total spores in the field. A total of 10 representative images were analyzed for each condition (test mixture). Germinated spores lose their refractivity due to the influx of water and are phase-dark while non-germinated spores are phase-bright.

FIG. 1 shows representative images from these tests. Image A represents spores that had been germinated using a nutrient-germinant composition and heated during the incubation period at 42° C. according to a preferred composition and preferred method of the invention. The darker spots show germinated spores, the lighter spots show non-germinated spores. Image B represents spores that had been germinated using a nutrient-germinant composition according to a preferred embodiment of the invention, but were incubated at ambient temperature (23° C.). Images C-D represent control spores that had not been treated with a nutrient germinant composition according to the invention, one having been incubated at 42° C. and one incubated at ambient temperature (23° C.).

As can be seen in FIG. 1, the "A" image shows significantly more germinated spores (dark spots) than the other images. Spores incubated with a nutrient-germinant composition according to a preferred embodiment invention in combination with a germination method according to a preferred embodiment of the invention show an apparent germination efficiency of 96.8% (Example 1, FIG. 1A). Control spores that had been incubated with a nutrient-germinant composition according to a preferred embodiment of the invention, but without using a germination method according to a preferred embodiment of the invention showed an apparent germination efficiency of 2.3% (Example 1, FIG. 1B). Similarly, spores that had not been incubated with a nutrient-germinant composition according to the invention showed an apparent activation efficiency of 1.2% and 2.6% at 42° C. and 23° C., respectively (Example 1, FIGS. 1C and 1D). Germinated spores in the samples not treated by preferred embodiments of the present method represent the small percentage of spores already germinated in the FreeFlow LF-88 Probiotic solution. This example demonstrates that spore germination is significantly increased when a nutrient-germinant composition and incubation method according to preferred embodiments of the invention are used together.

Example 2

Another set of incubation tests were run using the same test mixture/incubation method (using the same nutrient-germinant composition and heated incubation, "Treated Spores, 42° C.") and control mixture/incubation method (no nutrient-germinant composition and no heat, "Non-treated Spores, 23° C.") as described above in Example 1 were repeated, but different tests were run to compare the efficacy of the test mixture according to preferred embodiments of the invention as compared to the control mixture. Additionally, two other mixtures were tested—one in which the nutrient-germinant composition of Example 1 was used but without heat ("Treated Spores, 23° C.") and one in which no nutrient-germinant was used but the spores were heated ("Non-Treated Spores, 42° C."). Briefly, spores were incubated at 42° C. or 23° C. for 1 hour with or without treatment with a preferred nutrient-germinant composition. After incubation, the spores from 1 mL of each reaction were pelleted at 14K RPM for 3 min at 23° C. and resuspended in 1 mL of Butterfield's buffer. Approx. $6 \times 10^5$ CFUs (0.02 mL) were added to 0.980 mL of Davis minimal media (containing 3% glucose as a carbon source and trace elements) with an excess of D-alanine. D-alanine is a potent inhibitor of L-amino acid-mediated germination.

Approx. $1.2 \times 10^5$ CFUs were added to each of four wells of a PreSens OxoPlate. PreSens OxoPlates use optical oxygen sensors to fluorescently measure the oxygen content of the sample using two filter pairs (excitation: 540 nm, emission: 650 nm and excitation: 540, emission: 590 nm). Controls were performed as described by the manufacturer and measurements were taken on a BioTek 800FLx fluorescence plate reader. Time points were taken every 10 minutes for 24 hours at 37° C. with continual shaking and data was processed to determine the partial pressure of oxygen (pO$_2$) using the following formula:

$$pO_2=100*[(K_0/IR)-1(K_0/K_{100})-1]$$

Spores that have germinated and continue to divide and grow as vegetative cells consume oxygen as part of their metabolic growth. Oxygen consumption is represented by a drop in pO$_2$. Presumably, the growth that is observed is due to the outgrowth and vegetative growth of spores germinated by the present invention. The pO$_2$ levels for these tests are shown in FIG. 2.

Figure 2:
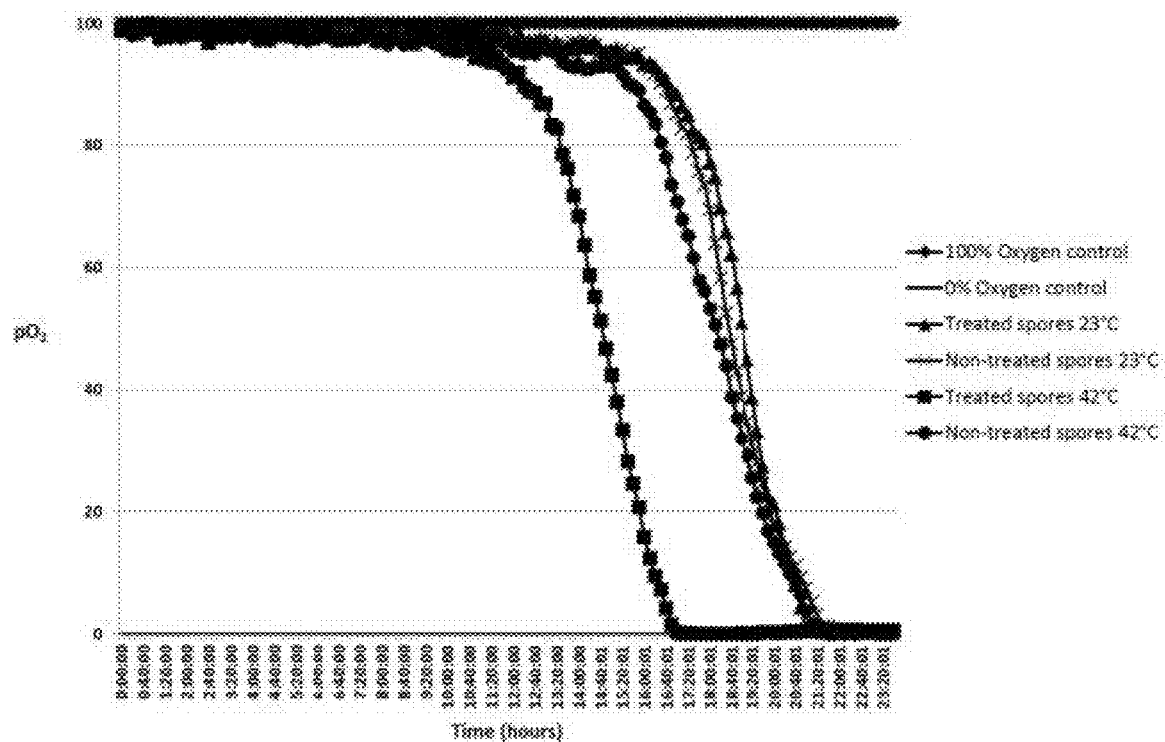
FIG. 2 is a graph showing $pO_2$ test data to demonstrate germination levels using a composition and method according to a preferred embodiment of the invention compared to control tests.

As shown in FIG. 2, incubation with the test mixture and method according to preferred embodiments of the invention (Treated spores 42° C., using both the nutrient-germinant composition and heating) resulted in spores that began vegetative growth 4 hours faster than the control spore mixtures that had not been treated or heated according to preferred embodiments of the invention or had been either treated with a nutrient-germinant composition or heated, but not both together. The growth seen in the control experiments presumably represents the approx. 2% of germinated spores present in FreeFlow LF-88 Probiotic (see EXAMPLE 1). This example further indicates that spore germination is significantly increased when a nutrient-germinant composition and incubation method according to preferred embodiments of the invention are used.

Example 3

Another set of incubation tests were run using a similar test and control mixture and incubation method as described above in Example 1. Briefly, LF-88 was added to 10 mLs of distilled water at a final concentration of approx. 10$^8$ CFU/mL. Samples were incubated at various temperatures to show the efficacy of the test method according to preferred embodiments of the invention as compared to the control mixture. Reactions were prepared with the nutrient-germinant composition described in Example 1 ("Treated spores" in FIG. 3) and incubated at 23° C. (ambient temperature, no heating), 32° C., 42° C., or 60° C. A control reaction was incubated at ambient room temperature with no nutrient-germinant composition. After one hour of incubation, 1 mL of each reaction was pelleted at 14K RPM for 3 min at 23° C. and resuspended in Butterfield's buffer. Approx 6×10$^5$ CFUs (0.02 mL) were added to 0.980 mL of Davis minimal media (containing 3% glucose as a carbon source and trace elements) with an excess of D-alanine.

Approx. 1.2×10$^5$ CFUs were added to each of four wells of a PreSens OxoPlate. Controls were performed as described by the manufacturer and measurements were taken on a BioTek 800FLx fluorescence plate reader using two filter pairs (excitation: 540 nm, emission: 650 nm and excitation: 540, emission: 590 nm). Time points were taken every 10 minutes for 24 hours at 37° C. with continual shaking and data was processed to determine the partial pressure of oxygen (pO$_2$). The pO$_2$ levels for these tests are shown in FIG. 3.

Figure 3:
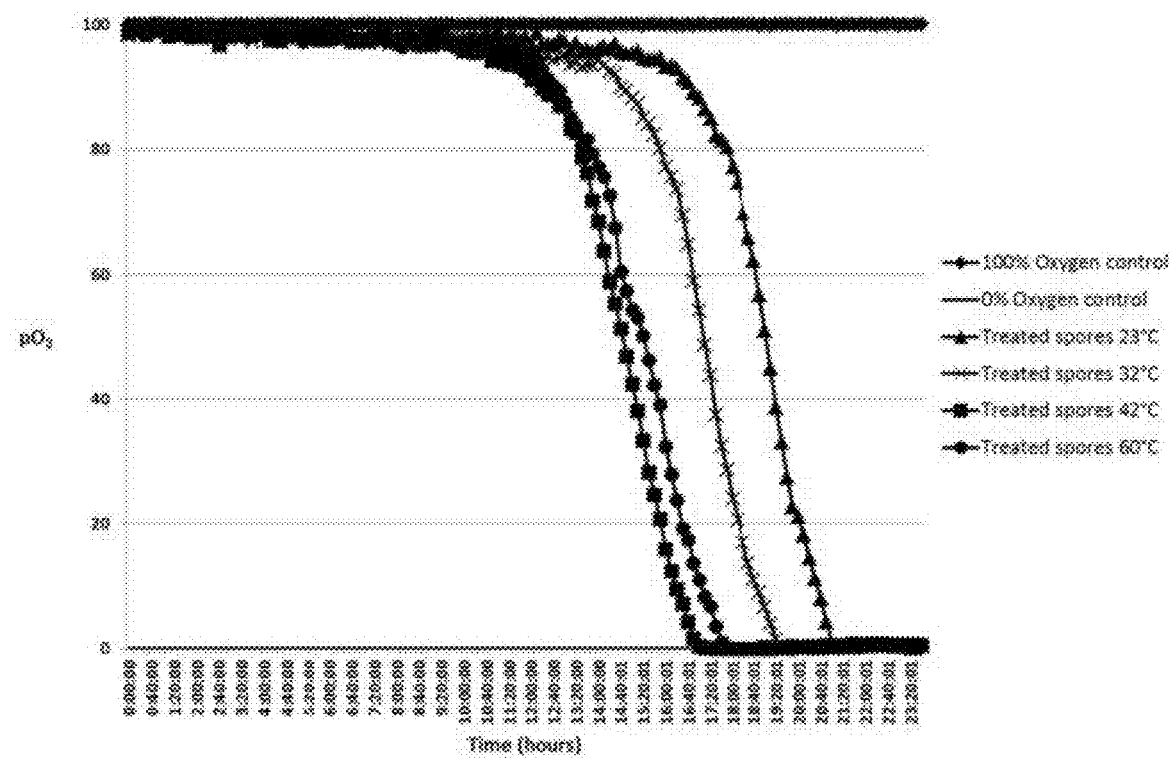
FIG. 3 is a graph showing $pO_2$ test data to demonstrate germination levels using a composition and varied methods according to preferred embodiments of the invention compared to control tests.

As shown in FIG. 3, incubation using a nutrient-germinant composition and heating according to preferred embodiments of the invention resulted in spores that began vegetative growth hours before the control. Spores treated with the nutrient-germinant composition but not heated are comparable to the control mixture. Spores treated with the nutrient-germinant composition that were incubated at a temperature below the preferred range of range of 35-55° C. according to one embodiment of the invention (represented by the "Treated spores 32° C." curve) begin vegetative growth faster than control experiments, but not as fast as spores treated at elevated temperatures within the preferred ranges according to the invention. Spores treated with a nutrient-germinant composition and incubated at a temperature within the most preferred range of 41° C. to 44° C. according to an embodiment of the invention showed the best results, being the first to begin vegetative growth and beginning growth 4 hours faster than the control. As seen in previous examples, growth seen in the no-treatment control experiment presumably represents the approx. 2% of germinated spores present in FreeFlow LF-88 Probiotic (see EXAMPLE 1). This example further indicates that spore germination is significantly increased when a nutrient-germinant composition and incubation method according to preferred embodiments of the invention are used.

Those of ordinary skill in the art will also appreciate upon reading this specification and the description of preferred embodiments herein that modifications and alterations to the device may be made within the scope of the invention and it is intended that the scope of the invention disclosed herein be limited only by the broadest interpretation of the appended claims to which the inventors are legally entitled.

We claim:

1. A nutrient-germinant composition to aid in bacteria spore germination, the composition comprising:
   one or more L-amino acids;
   one or more buffers comprising a phosphate buffer, HEPES, Tris base, or a combination thereof;
   one or more industrial preservatives comprising one or more of propylparaben, methylparaben, methyl chloro isothiazolinone, and methyl isothiazolinone;
   optionally D-glucose, optionally D-fructose, or optionally both D-glucose and D-fructose;
   optionally a source of potassium ions; and
   wherein the composition is heated to a temperature in a range of 38° C. to 60° C.

2. The nutrient-germinant composition according to claim 1 wherein the L-amino acid is L-alanine, L-asparagine, L-valine, L-cysteine, a hydrolysate of soy protein, or a combination thereof.

3. The nutrient-germinant composition according to claim 1 wherein the composition is a concentrated liquid and comprises 8.9-133.5 g/L each of one or more L-amino acids.

4. A nutrient-germinant composition to aid in bacteria spore germination, the composition comprising:
   one or more L-amino acids;
   one or more buffers comprising a phosphate buffer, HEPES, Tris base, or a combination thereof;
   one or more industrial preservatives;
   optionally D-glucose, optionally D-fructose, or optionally both D-glucose and D-fructose;
   optionally a source of potassium ions;
   spores of one or more *Bacillus* species;
   a germination inhibitor; and
   wherein the composition is heated to a temperature in a range of 38° C. to 60° C.

5. The nutrient-germinant composition according to claim 4 wherein the germination inhibitor comprises sodium chloride, D-alanine, or a combination thereof.

6. The nutrient-germinant composition according to claim 5 wherein the composition comprises 29 g/L to 117 g/L sodium chloride.

7. The nutrient-germinant composition according to claim 5 wherein the composition comprises 8 g/L to 116 g/L D-alanine.

8. The nutrient-germinant composition according to claim 4 wherein the one or more industrial preservatives comprise one or more of propylparaben, methylparaben, methyl chloro isothiazolinone, and methyl isothiazolinone.

9. The nutrient-germinant composition according to claim 8 wherein the composition comprises 0.8-3.3 g/L total of the one or more industrial preservatives.

10. The nutrient-germinant composition according to claim 3 wherein the composition comprises 0.8-3.3 g/L total of the one or more industrial preservatives.

11. The nutrient-germinant composition according to claim 10 wherein the L-amino acid is L-alanine, L-asparagine, L-valine, L-cysteine, a hydrolysate of soy protein, or a combination thereof.

12. A concentrated liquid nutrient-germinant composition to aid in bacteria spore germination, the composition comprising:
one or more L-amino acids;
one or more buffers comprising a phosphate buffer, HEPES, Tris base, or a combination thereof;
one or more industrial preservatives;
optionally D-glucose, optionally D-fructose, or optionally both D-glucose and D-fructose;
optionally a source of potassium ions;
wherein the composition is heated to a temperature in a range of 38° C. to 60° C.;
and
wherein the one or more buffers comprise 10-36 g/L monosodium phosphate, or 30-90 g/L disodium phosphate, or 15-61 g/L Tris base, or 32.5-97.5 g/L HEPES, or a combination thereof.

13. The nutrient-germinant composition according to claim 3 wherein the one or more buffers comprise 10-36 g/L monosodium phosphate, or 30-90 g/L disodium phosphate, or 15-61 g/L Tris base, or 32.5-97.5 g/L HEPES, or a combination thereof.

14. The nutrient-germinant composition according to claim 4 wherein the *Bacillus* species is *Bacillus licheniformis, Bacillus subtilis, Bacillus amyloliquiefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus pumilus, Bacillus simplex*, and *Bacillus sphaericus*, or a combination thereof.

15. The nutrient-germinant composition according to claim 4 wherein the *Bacillus* species are capable of producing enzymes that aid in the breakdown of organic matter in the digestive tract of a consuming animal.

16. The composition according to claim 15 wherein the enzymes comprise amylase, protease, lipase, esterase, urease, cellulase, xylanase, or a combination thereof.

17. The composition according to claim 12 wherein the composition comprises:
8.9-133.5 g/L each of one or more L-amino acids;
0.8-3.3 g/L total of the one or more industrial preservatives;
optionally 18-54 g/L of D-glucose, D-fructose, or a combination thereof; and
7.4-22.2 g/L of KCl.

18. The nutrient-germinant composition according to claim 17 wherein the L-amino acid is L-alanine, L-asparagine, L-valine, L-cysteine, a hydrolysate of soy protein, or a combination thereof.

19. The composition of claim 17 wherein the phosphate buffer comprises 10-36 g/L of monosodium phosphate and 30-90 g/L of disodium phosphate.

20. The composition according to claim 1 wherein the composition is a concentrated liquid wherein:

the one or more L-amino acids comprise 8.9-133.5 g/L L-alanine;
the one or more industrial preservatives comprise 0.8-3.3 g/L total of one or more of methyl chloro isothiazolinone and methyl isothiazolinone;
the one or more buffers comprise 10-36 g/L monosodium phosphate and 30-90 g/L disodium phosphate;
18-54 g/L of D-glucose, D-fructose, or a combination thereof; and
7.4-22.2 g/L of KCl.

21. The nutrient-germinant composition according to claim 1 wherein methylparaben is one of the one or more industrial preservatives and propyl paraben is not one of the one or more industrial preservatives.

22. The nutrient-germinant composition according to claim 1 wherein methyl chloro isothiazolinone or methyl isothiazolinone is one of the one or more industrial preservatives.

23. The nutrient-germinant composition according to claim 22 further comprising spores of one or more *Bacillus* species that are not separately heat activated prior to addition to the composition.

24. The nutrient-germinant composition according to claim 22 wherein the composition does not include fructose or glucose.

25. The nutrient-germinant composition according to claim 12 wherein the one or more industrial preservatives comprise methyl chloro isothiazolinone and methyl isothiazolinone.

26. The nutrient-germinant composition according to claim 17 further comprising water to dilute the composition to 4% to 10% of the concentrated amounts and wherein the buffers comprise monosodium phosphate and disodium phosphate.

27. The nutrient-germinant composition of claim 17 wherein the phosphate buffer comprises 15-30 g/L of monosodium phosphate and 30-90 g/L of disodium phosphate.

28. The nutrient-germinant composition according to claim 17 wherein the temperature range is 41° C. to 44° C.

29. The nutrient-germinant composition according to claim 20 wherein the temperature range is 41° C. to 44° C.

30. The nutrient-germinant composition according to claim 24 wherein the temperature range is 41° C. to 44° C.

31. The nutrient-germinant composition according to claim 1 wherein the buffers comprise monosodium phosphate and disodium phosphate;
wherein the industrial preservative comprises methylparaben; and
wherein the composition does not include fructose or glucose.

32. The nutrient-germinant composition according to claim 26 wherein the composition does not include fructose or glucose.

33. A nutrient-germinant composition to aid in bacteria spore germination, the composition comprising:
L-alanine;
one or more buffers comprising monosodium phosphate or disodium phosphate or both;
one or more industrial preservatives comprising propylparaben, methylparaben, methyl chloro isothiazolinone, methyl isothiazolinone, or a combination thereof; and
a source of potassium ions;
wherein the composition is heated to a temperature in a range of 38° C. to 50° C. at or near a point-of-use consisting of animal bedding, animal feed, or animal drinking water, a wastewater system, or a dr 34. The nutrient-germinant composition according to claim 33 wherein the composition does not include fructose or glucose.

35. The nutrient-germinant composition according to claim 34 wherein the source of potassium ions is potassium chloride.

36. The nutrient-germinant composition according to claim 1 wherein the composition is heated for 20 to 60 minutes.

37. The nutrient-germinant of claim 36 wherein the industrial preservative comprises methyl chloro isothiazolinone, or methyl isothiazolinone, or both.

38. The nutrient-germinant composition according to claim 36 further comprising spores of one or more *Bacillus* species that are not separately heat activated prior to addition to the composition.

39. The nutrient-germinant composition of claim 1 wherein the L-amino acids comprise a hydrolysate of soy protein.

40. The nutrient-germinant composition according to claim 4 wherein the spores of the one or more *Bacillus* species are not separately heat activated prior to addition to the composition.

41. The nutrient-germinant composition according to claim 40 wherein the one or more buffers comprise monosodium phosphate and disodium phosphate;
    wherein the industrial preservative comprises methylparaben.

42. The nutrient-germinant composition according to claim 41 wherein the temperature range is 41° C. to 44° C. and the composition is heated for 2-10 minutes.

43. The nutrient-germinant composition according to claim 42 wherein the composition does not include fructose or glucose.

44. The nutrient-germinant composition according to claim 1 wherein the one or more buffers comprise monosodium phosphate and disodium phosphate;
    wherein methylparaben is one of the one or more industrial preservatives.

45. The nutrient-germinant composition according to claim 44 wherein the temperature range is 41° C. to 44° C. and the composition is heated for 2-10 minutes.

46. The nutrient-germinant composition according to claim 45 wherein the composition does not include fructose or glucose.

47. The nutrient-germinant composition according to claim 46 wherein the composition is a concentrated liquid comprising 8.9-133.5 g/L each of one or more L-amino acids; and
    0.8-3.3 g/L methylparaben.

48. The nutrient-germinant composition according to claim 44 wherein the composition is a concentrated liquid comprising 8.9-133.5 g/L each of one or more L-amino acids;
    0.8-3.3 g/L methylparaben; and
    and the composition is heated for 2-10 minutes.

* * * * *